United States Patent [19]

Folkman et al.

[11] Patent Number: 5,202,311
[45] Date of Patent: Apr. 13, 1993

[54] STABILIZED FGF COMPOSITION

[75] Inventors: Moses J. Folkman, Brookline; Yuen Shing, Randolph, both of Mass.

[73] Assignee: Children's Medical Center Corporation, Boston, Mass.

[21] Appl. No.: 524,144

[22] Filed: May 15, 1990

Related U.S. Application Data

[63] Continuation-in-part of Ser. No. 382,263, Jul. 10, 1989, Pat. No. 5,175,147, which is a continuation-in-part of Ser. No. 234,966, Aug. 18, 1988, abandoned.

[51] Int. Cl.$^5$ .................... A61K 37/02; A61K 37/36; A61K 31/715
[52] U.S. Cl. ........................ 514/12; 514/23; 514/53; 514/21; 530/399; 536/1.11; 536/122
[58] Field of Search ................ 514/12, 23, 21, 53; 530/399; 536/1.1, 122

[56] References Cited

U.S. PATENT DOCUMENTS 4,912,093  3/1990  Michaeli ........................ 514/21

FOREIGN PATENT DOCUMENTS

| 230023 | 7/1987 | European Pat. Off. |
| 345660 | 12/1989 | European Pat. Off. |
| 360006 | 3/1990 | European Pat. Off. |
| 378852 | 7/1990 | European Pat. Off. |
| 406856 | 1/1991 | European Pat. Off. |
| 8905645 | 8/1989 | World Int. Prop. O. |
| PCTUS88/01660 | 9/1989 | World Int. Prop. O. |
| 8912464 | 12/1989 | World Int. Prop. O. |
| WO 90/01941 | 3/1990 | World Int. Prop. O. |
| 9010456 | 9/1990 | World Int. Prop. O. |

OTHER PUBLICATIONS

Senoo, et al., Biochemical and Biophysical Research Communications, 151:701–708 (1988).
Szabo, et al., Digestive Diseases and Sciences 34(8):1323 (1989).
Vlodavsky, et al., PNAS (USA), 64:2292–2296 (1987).
Folkman, et al., Amer. J. Pathol. 130:393–400 (1988).
Klagsburn, et al., PNAS 82:805–809 (1985).
Tasman-Jones, et al., The American Journal of Medicine, 86(suppl. 6A):5–9 (1989).
Szabo, et al., The American Journal of Medicine 86 (suppl. 6A):23–31 (1989).
Konturek, et al., The American Journal of Medicine 86 (suppl. 6A):32–37 (1989).
Guslandi, The American Journal of Medicine 86 (suppl. 6A):45–48 (1989).
Shepherd, et al., The American Journal of Medicine 86 (suppl. 6A):49–54 (1989).
Szabo, et al., Proc. Soc. Exp. Biol. Med., 185:493–497 (1987).
Folkman, et al., Science, 235:442–447 (1987).
Connolly, et al., J. Clin. Invest. 84:1470–1478 (1989).

(List continued on next page.)

Primary Examiner—F. T. Moezie
Attorney, Agent, or Firm—David G. Conlin; David S. Resnick; Gregory D. Williams

[57] ABSTRACT

Methods for stabilizing fibroblast growth factor (FGF) in heat, acid and/or proteolytic environments are provided. Such methods comprise combining or otherwise complexing FGF with a salt of sucrose octasulfate (SOS) and in particular with the aluminum (sucralfate) or potassium salts thereof. The present invention also provides FGF-stable compositions comprising SOS and FGF. Such compositions can be used in the treatment of FGF-responsive diseases including the treatment of wounds and ulcerative conditions of the gastrointestinal tract. The present invention also provides various diagnostic protocols employing SOS as well as diagnostic kits with SOS as a component thereof. Finally, the present invention provides methods of purifying FGF with SOS.

13 Claims, 4 Drawing Sheets

OTHER PUBLICATIONS

S. Dai, et al., Pediatric Research, 19:916–918 (1985).
D. Gospodarowicz, et al., Proc. Natl. Acad. Sci. USA, 86:7311–7315 (1989).
T. Kurokawa, et al., FEBS Letter 213(1):189–194 (1987).
Y. Shing, et al., Science, 223:1296–1299 (1984).
D. Goaspodarowicz, et al., Journal of Cellular Physiology, 128:475–484 (1986).
P. Kirkegaard, Gastroenterology 85:1277–1283 (1983).
G. Conn, et al., Proc. Natl. Acad. Sci. USA, 87:1323–1327 (1990).
M. Iwane, et al., Biochemical and Biophysical Research Communications, 146(2):470–477 (1987).
N. Ferrara, et al., Biochemical and Biophysical Research Communications 161(2):851–858 (1989).
J. Folkman et al., Science, 243:1490–1493 (1989).
Shing, et al., Analytical Biochemistry, 185:108–111 (1990).
Folkman, et al., Journal of Cell Biology vol. 111, No. 5, p. 223, column 1. abstract 1244 (1990).
Li, W. W. et al., Investigative Ophthalmology & Visual Science, vol. 32 No. 4, p. 955, column 2, abstract 1412-6:45 (1991).

STABILIZED FGF COMPOSITION

The present application is a continuation-in-part of U.S. Ser. No. 07/382,263 filed Jul. 10, 1989, now U.S. Pat. No. 5,175,147, which is a continuation-in-part of U.S. Ser. No. 07/234,966 filed Aug. 18, 1988, now abandoned.

In accordance with the present invention, there is provided a method for stabilizing fibroblast growth factor (FGF) in heat, acid and/or proteolytic environments by combining or otherwise complexing FGF with a salt of sucrose octasulfate (SOS) and in particular with the aluminum (sucralfate) or potassium salts thereof. The present invention also relates to FGF-stable compositions comprising SOS and FGF. This composition can be used in the treatment of FGF-responsive diseases including the treatment of wounds and ulcerative conditions of the gastrointestinal tract. The present invention also relates to the use of SOS in various diagnostic protocols and as a component of diagnostic kits. Finally, the present invention relates to the use of SOS to purify FGF.

BACKGROUND OF THE INVENTION

Ulcerating diseases of the gastrointestinal tract, commonly referred to as peptic ulcers, are diseases in which there is a defect in the epithelium of the gastrointestinal tract. This type of defect usually occurs through the combined action of hydrochloric acid and pepsin. By definition, peptic ulcers penetrate to at least the submucosa; more superficial lesions are referred to as erosions. Peptic ulcers may occur in many locations of the gastrointestinal tract including the stomach, duodenum or esophagus, in Meckel's diverticulum, at the sight of a surgically created anastomosis, and, rarely, in the upper jejunum.

Twenty years ago, treatment of peptic ulceration consisted of bedrest, a bland diet, antacids, and/or surgical removal of the affected area. More recently, $H_2$-receptor antagonists have been used in the treatment of peptic ulcers. The two most commonly used $H_2$-receptor antagonists are ranitidine and cimetidine, both of which act therapeutically by inhibiting gastric acid secretion. The effectiveness and unwanted effects of these two antagonists has been extensively studied, e.g. by Thomas et al., in *Clinics in Gastroenterology*. Volume 13, Number 2, at pages 501–529.

While treatment with these antagonists has been widespread and relatively successful, many peptic ulcers do not respond to $H_2$-receptor antagonist therapy. For example, while the reasons are not clearly understood, some 20 to 30% of duodenal ulcers do not heal after four to six weeks of therapy with either cimetidine or ranitidine. Moreover, recurrence or relapse of the ulcerating condition is not uncommon with $H_2$-receptor antagonists.

Sucralfate has also been used as an ulcer curative agent with minimal side effects. Sucralfate is believed to influence multiple mechanisms of gastrointestinal protection and repairing/healing including i) adsorption of pepsin and bile acids, ii) cytoprotective activity of the gastro stimulation of mucus secretion and bicarbonate secretion by the gastric mucosa, iii) protection against damage to the prolifactive zone, and iv) protection of vascular integrity. Although major advances have been made in the understanding of how sucralfate prevents erosions and ulcers, and how it accelerates the healing of ulcers, a major gap exist in the elucidation of chronic therapeutic actions of this drug.

Fibroblast growth factor (FGF), has been shown to be a potent angiogenic factor which, inter alia. is responsible for neovascularization in wound healing. There are two types of FGF, acidic fibroblast growth factor (aFGF) and basic fibroblast growth factor (bFGF). aFGF and bFGF are, however, acid and/or heat labile. Thus, the use of FGF in acid and/or heat environments such as in the treatment of peptic ulcers requires that it be stabilized to that environment in order to maximize its therapeutic value.

Recently, however, in PCT application serial no.: PCT/US89/03467, published Mar. 8, 1990, the disclosure which is hereby incorporated by reference, there is disclosed certain acid-resistant FGF compositions including recombinant FGF in combination with i) stabilizing agents such as glycosaminoglycan, glucan sulfates and sulfated cyclodextrins, ii) antisecretory agents such as $H_2$-receptor antagonists, iii) cytoprotective agents, and iv) antacids. These novel compositions are disclosed as being extremely effective in the treatment of ailments in which FGF would be a potent medicament but for the acid and/or heat environment to which it is subjected.

There continues to be a need, however, for new ways of further stabilizing FGF so that its diagnostic potential and therapeutic potential in the treatment of gastrointestinal conditions, wounds, and the like can be realized.

SUMMARY OF THE INVENTION

In accordance with the present invention there is provided a method for stabilizing FGF, which comprises combining or otherwise complexing FGF with a salt of sucrose octasulfate (SOS), and in particular with the aluminum or potassium salts thereof. As used herein, "SOS" includes salts of sucrose octasulfate including, but not limited to the aluminum and potassium salts therof. The stabilized FGF composition of the present invention can be used to treat mammals having virtually any disease which is FGF-responsive, and particularly in diseases where there is an acid or heat environment, or in an environment where protelytic factors are present. Specifically, the composition of the present invention can be used in the treatment of ulcerating diseases of the gastrointestinal tract by administering to the patient an effective amount of FGF in combination with SOS together with a pharmaceutically acceptable carrier, vehicle or diluent. The composition is also useful in treating wounds where proteolytic agents would otherwise interfere with FGF's therapeutic value.

In accordance with another aspect of the present invention, it has been found that SOS has a higher affinity for FGF, thus making it useful in purifying FGF as well as useful in diagnostic applications where the presence and/or amount of FGF is important.

DETAILED DESCRIPTION OF THE INVENTION

Figure 1:
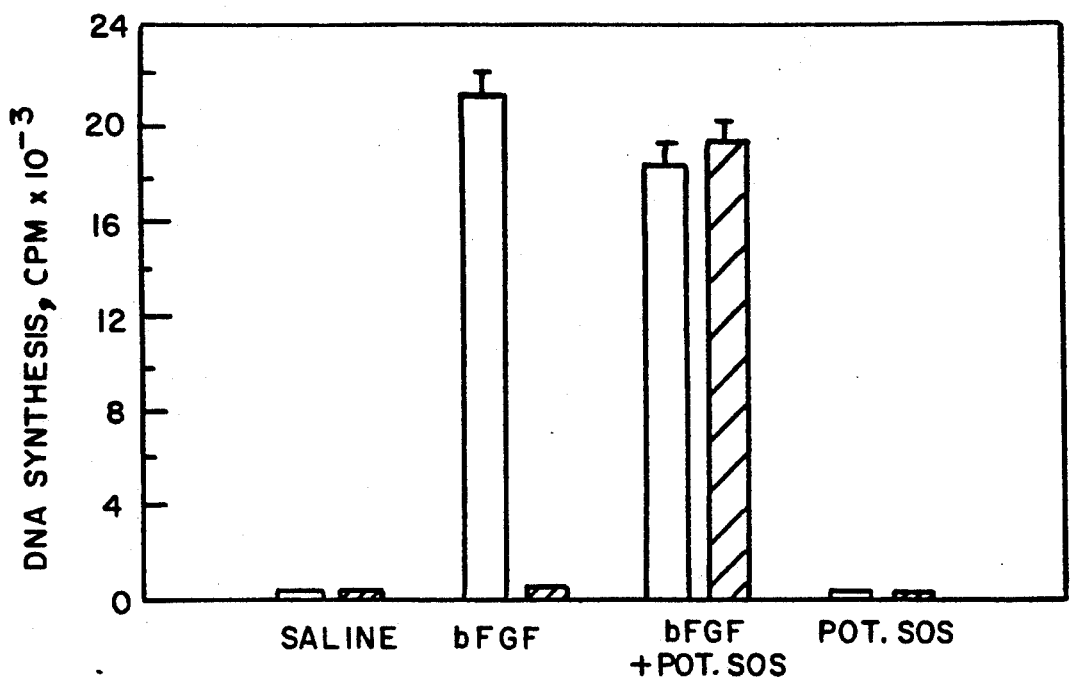
FIG. 1 illustrates the effect of high temperature on bFGF with and without SOS.

The present invention provides novel stable FGF compositions for the treatment and/or prevention of diseases in mammals which are responsive to FGF therapy. The present invention also provides for methods of purifying FGF as well as certain diagnostic applications where the presence and/or amount of FGF must be determined.

The method of treating FGF responsive diseases, in its simplest form, comprises administering to the mammal an effective amount of a stabilized FGF composition or a pharmaceutically acceptible salt thereof, wherein the stabilized composition comprises SOS in combination with FGF.

For example, various ulcerating diseases of the gastrointestinal tract may be treated by administering to the mammal an effective amount of the stabilized FGF composition. Such ulceraing diseases include regional ileitis, ulcerative colitis and peptic ulcer (either duodenal or gastric).

The stabilized FGF composition of the present invention can also be used to treat other conditions in mammals which would be responsive to FGF therapy but for the existence of an acidic, heat, and/or proteolytic environment. For example, in radiotherapy or chemotherapy of bladder cancer, there often results ulcerations of that organ's tissue which could be treated with FGF if the FGF were stabilized to acid environment found in the bladder. Wounds can also produce an acid and/or proteolytic environment which would respond to stabilized FGF composition of this invention. Other conditions in which there is an acid, heat, or proteolytic environment and which would otherwise be responsive to FGF therapy will be apparent to the skilled artisan, and include:

i) tissue injuries, burns, wounds, postoperative tissues, thrombosis, arteriosclerosis;

ii) musculo-skeletal conditions such as bone fractures, ligament and tendon repair, tendonitis and bursitis, skin conditions such as minor burns, cuts, lacerations, bed sores, slow-healing and chronic ulcers such as those seen in diabetics, and in tissue repair during ischaemia and myocardial infarction; and iii) retinopathies of the eye including diabetic retinopathy and neovascular glaucoma, skin disorders including psoriasis and retrolental fibroplasia, chronic inflammation, rheumatoid arthritis, and certain neoplasms that are highly angiogenic such as growth of certain benign and malignant tumors such as hemagiomas and angiofibromas, and solid tumors.

The stabilized FGF composition of the present invention may be a composition of SOS and either aFGF or bFGF. aFGF and bFGF useful in practicing the present invention may be derived from a number of sources including mammals such as human, bovine, monkey, swine and equine.

The preferred stabilized FGF composition is one which includes a modified FGF such as a purified recombinant human basic FGF (rhbFGF) protein in which a mutation is induced ("mutein") by changing one or more of the four cysteines present at amino acid residues 25, 69, 87, and 92 of the mature protein to serine. In numbering the human bFGF-constituent amino acids, the N-terminal Pro comprises the first amino acid. The most preferred FGF is the rhbFGF mutein CS23, the structure of which is more fully described in Senoo et al., Biochemical and Biophysical Research Communications, Vol. 151, No. 2, 701–708 (1988) an in U.S. Ser. No. 161,123, filed Feb. 18, 1988, which corresponds to EP-281,822 A2, the disclosures of which are hereby incorporated by reference herein. Other muteins which can be used in practicing the present invention and which are also described in these references include muteins in which amino acid(s) have been added, and where constituent amino acid(s) have been deleted or substituted.

Stabilized FGF compositions in accordance with the present invention have been found to be highly stable in acid, heat and proteolytic environments. Native mammalian FGF and FGF which is recombinantly modified as above to be acid-resistant are very low in toxicity.

The two preferred forms of sucrose octasulfate which may be used to stabilize FGF are potassium SOS and aluminum SOS (sucralfate). Which form of sucrose octasulfate is used in preparing the preferred stabilized FGF composition will depend on a number of factors including route of administration, requirement for solubilization, and the like. For treatment of gastrointestinal diseases, the preferred SOS is aluminum SOS (sucralfate) because it will not absorb into the blood stream.

The preferred route of administration of the stabilized FGF composition of the present invention will also depend on a number of factors including the condition being treated and patient convenience. For example, when used to treat ulcerating wounds of the bladder which are induced, for example, by radiation treatment or chemotherapy, then the stabilized FGF composition may be administered by urethral catheter. In treating ulcerating wounds of the gastrointestina tract, the preferred route of administration is oral, e.g. by tablet, capsule, lozenge or chewable gum. Other routes of administration for diseases of the gastrointestinal tract include rectal, by enema and parenteral.

Preparation of the stabilized FGF composition for administration is accomplished by conventional techniques. For example, tablets and capsules are prepared by employing additives such as pharmaceutically acceptable carriers (e.g. lactose, corn starch, light silicic anhydride, microcrystalline cellulose, sucrose), binders (e.g. alpha-form starch, methylcellulose, carboxymethylcellulose, hydroxypropylcellulose, hydroxypropylmethylcellulose, polyvinylpyrrolidone), disintegrating agents (e.g. carboxymethylcellulose calcium, starch, low substituted hydroxypropylcellulose), surfactants (e.g. Tween 80 (Kao-Atlas), Pluronic F68 (Asahi Denka, Japan); polyoxyethylene-polyoxypropylene copolymer, antioxidants (e.g. L-cysteine, sodium sulfite, sodium ascorbate), lubricants (e.g. magnesium stearate, talc), and the like.

Rectal preparations are also prepared by conventional techniques, for example, by employing an oleaginous base such as a higher fatty acid glyceride (e.g, cacao butter of the natural origin, Witepsols (a semisynthetic base, (Dynamite Nobel, Federal Republic of Germany)), a medium fatty acid glyceride (e.g. Miglyols (Dynamite Nobel)) or a vegetable oil (e.g., sesame oil, soybean oil, corn oil, cottonseed oil, olive oil).

When the composition is formulated into an injectable aqueous solution, the solution is prepared by conventional methods using a solvent such as an aqueous solvent (e.g., distilled water, physiological saline, Ringer's solution), or oily solvent (e.g., sesame oil, olive oil).

If desired, on or more additives may be employed. Such additives include a dissolution aid (e.g. sodium salicylate, sodium acetate), buffer (e.g., sodium citrate, glycerine), isotonizing agent (e.g., glucose, invert sugar), stabilizers (e.g., human serum albumin, polyethylene glycol), preservative (e.g., benzyl alcohol, phenol) or analgesics (e.g., benzalkonium chloride, procaine hydrochloride). SOS in its potassium salt is preferred when it is to be used intravenously because of solubility.

When the composition is formulated into a solid preparation, the preparation can be produced by routine methods using, for example, a diluent (e.g., distilled water, physiological saline, glucose), excipient (e.g., carboxymethylcellulose (CMC), sodium arginate), preservative (e.g., benzyl alcohol, benzalkonium chloride, phenol), or analegesics (e.g., glucose, calcium gluconate, procaine hydrochloride). The preferred form to be used is sucralfate.

The amount of the FGF component of the composition is remarkably small when compared to other pharmaceutical agents such as the $H_2$-blockers, and depends on a number of factors including the condition being treated, whether or not it is used alone or in conjunction with antisecretory agents, cytoprotective agents and antacids, and the amount of food intake by the patient.

For example, when used to treat ulcerating diseases of the gastrointestinal tract in human adult patients, the amount of the FGF protein component of the composition to be administered orally is generally between about 0.1 μg and 30 mg per day, preferably between about 0.1 μg and 10 mg, more preferably between about 1.0 μg and 3 mg per day, and most preferably from about 10 μg to 300 μg per day. For oral administration, 10 μg to 150 μg of the rhbFGF mutein CS23 or its salt may be formulated with sucralfate (generaly between about 10 mg to 1000 mg of sucralfate) as a tablet or a capsule together with a pharmaceutically acceptable carrier, diluent or other suitable vehicle. Such a formulation is beneficially administered one to four times daily to bring the dosage within the preferred range.

For certain diseases of the lower gastrointestinal tract such as peptic ulcers and ulcerated colitis, it is preferred that the stabilized FGF composition be coated with an enteric copolymer such as hydroxypropylmethylcellulose phthalate, cellulose acetate phthalate or methacrylic acid copolymer to further protect the stabilized FGF from acid and digested enzymes such as pepsin. This coated composition thus passes into the gastrointestinal tract such as the digestive tract and alimentary canal where it therapeutic value is optimized.

The amount of SOS used to stabilize the FGF component of the FGF stabilized composition depends on a number of factors including solubility. The amount of sucralfate given to humans is indicative of the amount generally used in accordance with the present invention. For example, for oral administration, between about 0.1 to 6 g/day (preferably in divided doses) may be used in combination with the FGF component of the stabilized composition.

The SOS component of the present invention may also be in the form of other salts. Other salts which may be used include pharmaceutically acceptable cations, e.g., sodium, ammonium, trimethyl ammonium, and the like.

When FGF protein component is brought into contact with the sulfated dissaccharide in an aqueous medium, the ratio of SOS to the FGF protein component ranges from about 1 to 1 by weight, up to between 10,000 to 1 by weight.

The concentration of SOS in an aqueous medium ranges preferably from about 0.4 mg/ml to 400 mg/ml, more preferably from about 4 mg/ml to 40 mg/ml. The concentration of FGF in anaqueous medium ranges preferably from about 1 ng/ml to 5000 ng/ml, more preferably from about 10 ng/ml to 500 ng/ml.

For bringing the FGF protein component into contact with SOS in an aqueous medium, mere mixing of these materials in the aqueous medium accomplishes the purpose. As the aqueous medium, use is preferably made of distilled water, physiological saline, glucose solution, buffers such as phosphate buffer and Trihydroxymethyl-aminomethane-HCl buffer. The stabilized FGF composition can be used as it is, without separation or recovery.

By the processes described above, a highly stabilized composition of FGF is obtained, which composition can be safely used to treat mammals such as humans, rats, guinea pigs, dogs, mice, and the like.

Without wishing to be bound by theory, it is believed that the therapeutic effect of sucralfate (the aluminum salt of SOS) on gastric and duodenalulcers may depend on its ability to act as a sustained-release carrier and stabilizer of endogenous bFGF. In accordance with the present invention, it is believed that sucralfate extracts bFGF from normal mucosa and extracellular matrix and carries it in a biologically active form to the ulcer bed or other injured areas of the gastrointestinal tract. It has previously been shown that large quantities of bFGF are stored in the extracellular matrix (see Vlodavsky et al., P.N.A.S. (USA) 64:2292–2296 (1987) and Folkman et al., Amer. J. Pathol. 130:393–400 (1988)). This is consistent with the earlier report that administration of exogenous acid-stable bFGF facilitates rapid healing of induced chronic duodenal ulcers (see Szabo et al., Dig. Dis. Sci.:34:1323 (1989) and the above-referenced PCT Application Ser. No. PCT/US/03467). Thus in accordance with the present invention, it is believed that SOS stabilized FGF is effective in prolonging the biological activity of FGF in healing wounds, burns, ulcers, and the like.

In accordance with another embodiment, of the present invention there is provided methods for separating, purifying and identifying compounds such as FGF which have an affinity for sucralfate from a sample.

In general, the method comprises contacting a sample containing FGF (or other compounds which bind or otherwise complex with sucralfate) with a column comprising SOS as a component thereof. Any FGF present in the sample will bind to the sucralfate component of the column. FGF can thereof be eluted from the column with an appropriate high concentration of salt, or acidic acid.

In a variation of this embodiment, FGF may be contacted with a bi-affinity column of the type described in PCT Application No. PCT/US88/01660 International Publication No. WO89/08144, the disclosure of which is incorporated by reference, where sucralfate is substituted for the heparin component of the bi-affinity column.

In one preferred embodiment, a sucralfate sepharose column is made by mixing sucralfate and Sepharose beads (Pharmacia Fine Chemicals, Sweden) in a ratio of about 1 to 10 by weight.

The eluates which may be used in practicing the present invention will depend upon whether a standard affinity column is used or whether a bi-affinity column is used. In general, a high concentration salt solution such as sodium chloride is used to elute FGF from a standard affinity column. Other eluates include acetic acid. Preferred eluates will normally be aqueous solutions containing physiological salt and suitable buffering materials to maintain the pH at around 7. The preferred buffering composition is Tris, at a concentration of about 10 mm. For a bi-affinity column such as that discussed in the above-referenced PCT application, the eluates referred to therein may be used.

In accordance with yet another embodiment of the present invention there is provided the use of sucralfate and FGF in various diagnostic applications. For example, the amount of heparin-binding endothelial growth activity in urine is increased with bladder cancer (Chodak, G. W. et al. Cancer Res. 45:690–694,1985; and 46:5507–5510,1986). Thus, use of SOS in a specimen bottle would stabilize such activity present in the sample, thus allowing an increase in sensitivity and reliability of FGF as a cancer indicator.

Similarly, FGF in spinal fluid has been correlated with incidents of brain cancer. As above, SOS could be used to increase the sensitivity and reliability of this cancer assay by stabilizing the FGF present in the spinal fluid.

In its simplist form such assays comprise contacting the sample fluid suspected of containing FGF with SOS and analyzing the fluid for complexes of SOS and FGF. This could be done by measuring the incorporation of [$H^3$] thymidine into the DNA of BALB/c mouse 3T3 cells (Klagsbrun et al., PNAS 82;805–809, 1985), the disclosure of which is incorporated by reference herein.

SOS is also useful in stabilizing FGF found in various tissue culture, and has been found to be non-toxic to cells in vitro upto concentrations of 400 $\mu$g/ml. Thus SOS can be added as a component of tissue culture in order to stabilize any FGF endogenous to cells of the tissue culture.

The recombinant human basic FGF (rhbFGF) used in the following Examples I and II was produced in the manner described in Example 1, 3, 6 or 8 of EP-237,966 employing a transformant *Escherichia coli* K12 MM294/pTB669 (IFP 14532, FERM BP-1281).

rhbFGF mutein CS23 used in the following Example I was produced by the manner described in the above-referenced Biochemical and Biophysical Research Communications vol. 151, pates 701–708 (1988), and Reference Examples 1 and 2 and Examples 1, 6, 7 and 24 of U.S. patent application Ser. No. 161,123 which corresponds to EP-281,822 A2 employing a transformant *Escherichia coli* MM294/pTB 762 (IFO 14613, FERM BP-1645).

The invention will be further illustrated by reference to the following examples which will aid in the understanding of the present invention, but which are not to be construed as a limitation thereof.

EXAMPLE I

Stabilization of FGF by Sucralfate

A. Stabilization against Heat

A solution containing FGF was prepared by mixing 0.25 $\mu$g of human bFGF in 50 $\mu$l of Tris buffer containing 20 $\mu$g of BSA. This solution was incubated at 60° C. for 10 minutes in the presence and absence of 2 mg of potassium SOS. At the end of the incubation period, bFGF samples were diluted 20-fold with Tris buffer containing BSA (1 mg/ml) and analyzed for growth factor activity by measuring the incorporation of [$H^3$]thymidine into the DNA of BALB/c mouse 3T3 cells substantially as described in Klagsburn et al., P.N.A.S. (USA) 82:805–809(1985), the disclosure of which is hereby incorporated by reference herein.

As can be seen from FIG. 1, potassium SOS stabilizes FGF against high temperature. The activities recovered at the control temperature of 4° C. are shown as open bars.

B. Stabilization Against Acid

An acid solution containing FGF was prepared by mixing 0.5 $\mu$g of FGF in 60 $\mu$l of 1.5 M acetic acid containing 20 $\mu$g of BSA. This solution, which had a pH of about 2.2 was incubated at 37° C. for 30 minutes in the presence and absence of 2 mg of potassium SOS. At the end of the incubation period, bFGF samples were diluted and neutralized with Tris buffer containing BSA (1 mg/ml) and analyzed for growth factor activity as above. However, when the bFGF samples were acidified, they became insoluble and were therefore clarified by centrifugation. Both the supernatant and pellet which were subsequently solubilized in Tris buffer containing BSA (1 mg/ml) were then analyzed for growth factor activity.

Figure 2:
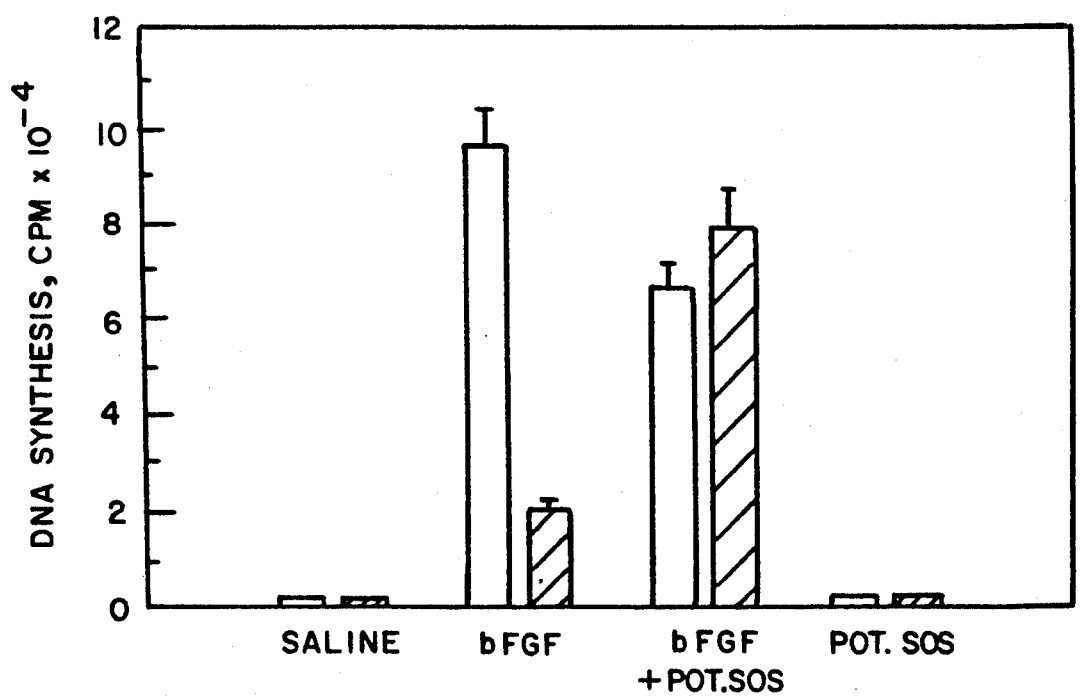
FIG. 2 illustrates the effect of acid on bFGF with and without SOS.

As can be seen from FIG. 2, potassium SOS stabilizes FGF against acid environment such as those found in the gastrointestinal tract. The activities recovered at a control pH (pH 7) are shown as open bars.

C. Stabilization Against Proteolytic Factors

A rhbFGF mutein CS23 solution (200$\mu$g/ml) was incubated at pH 2.3 and at 37° C. in the presence of pepsin (4$\mu$g/ml) for 20 hours with sucralfate. Sucralfate was added at a molar 1:10. The residual mitogenic activity was determined with bovine fetal heart endothelial cells ATCC CRL 1395.

Figure 3:
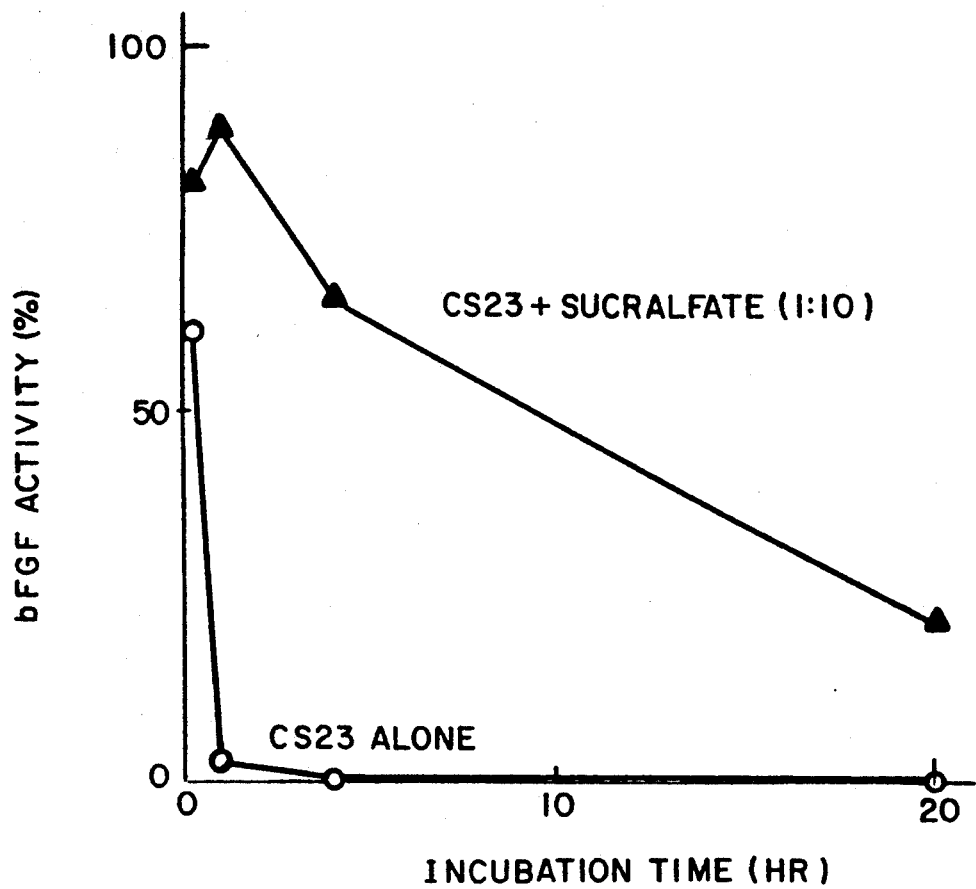
FIG. 3 illustrates the effect of pepsin on rhbFGF mutein CS23 with and without sucralfate.

As can be seen from FIG. 3, sucralfate protects rhbFGF mutein CS23 from the proteolytic effect of pepsin.

EXAMPLE II

Affinity of FGF Sucralfate

A. Heparin Affinity Chromatography

A Pharmacia fast performance liquid chromatography (FPLC) system was used to demonstrate the affinity of FGF for sucralfate as follows: 2.5 $\mu$g of bFGF in 0.1 ml of saline containing 0.1 mg of BSA was loaded onto a TSK-GEL Heparin 5PW column (3.5 cm × 8 mm inner diameter, obtained from Tosohaas, Phil., Pa.). The column was pre-equilibriated with 0.6 M NaCl, 10 mM Tris-HCl, pH 7 (Tris buffer). After loading, the column was rinsed with 10 ml of Tris buffer with 0.6 M NaCl. The bound activities were eluted with 4 ml of Tris buffer containing either 2 M NaCl or 78 mM potassium SOS at a flow rate of 0.5 ml/min. Fractions of 1 ml were collected and analyzed for growth factor activity as described in Example I.

Figure 4:
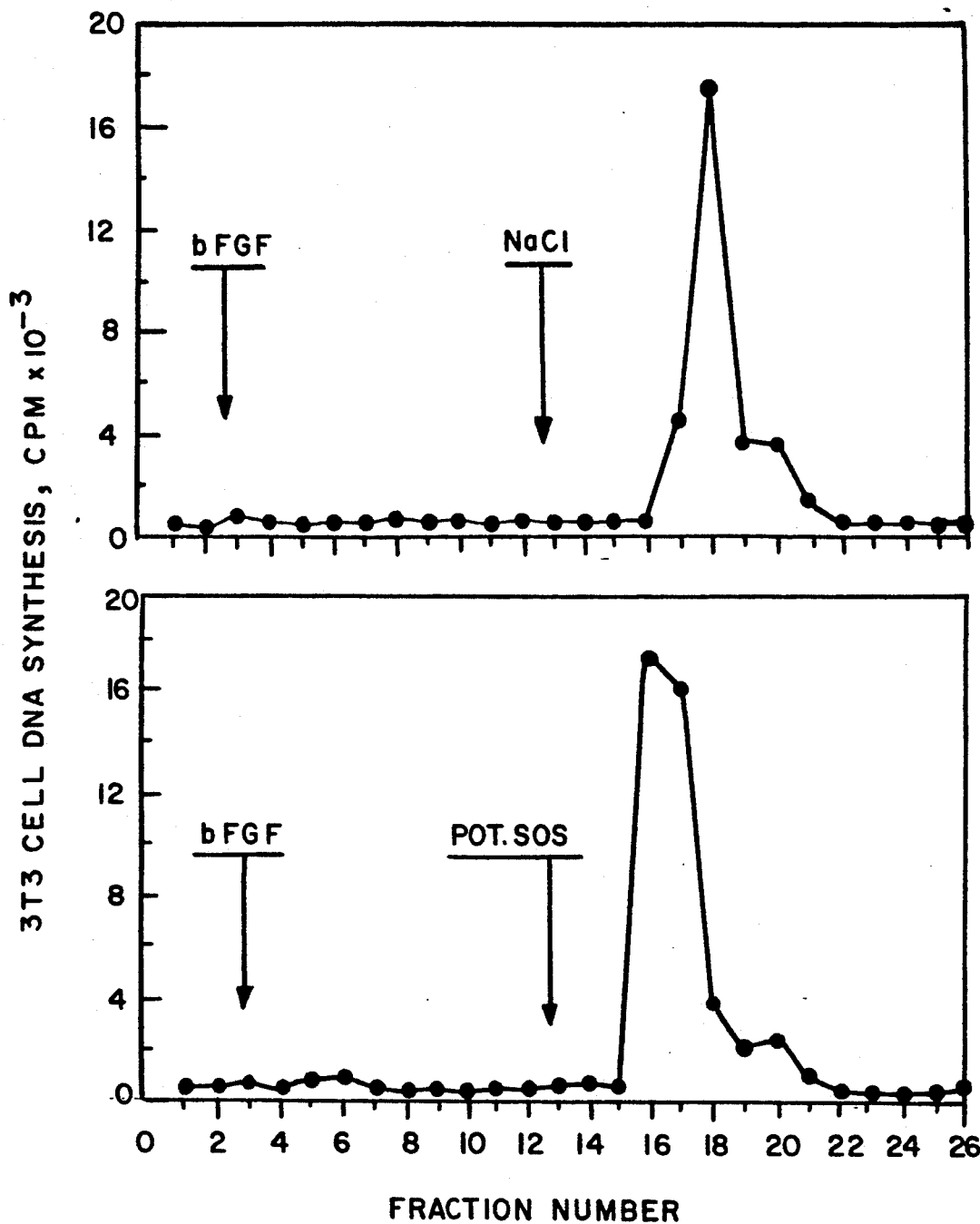
FIG. 4 illustrates the affinity of SOS for bFGF by its ability to uncouple bFGF from heparin as compared with 2 M NaCl.

As shown in FIG. 4 potassium SOS uncouples bFGF from a heparin-Sepharose column at 78 mM. It further shows that the mitogenic activity recovered by SOS was at least comparable to that recovered by 2 M NaCl (FIG. 4, upper panel). Since previous studies demonstrated that bFGF adheres tightly to immobilized heparin (see Shing et al., Science 223:1296–1298 (1984) and Klagsburn et al., supra.) and could be eluted with high concentrations of NaCl (i.e., 1.5 M), it appears that bFGF has equal or greater affinity for sucralfate as compared with heparin.

B. Sucralfate Sepharose Chromatography

A sucralfate-Sepharose column was prepared by mixing 0.1 g of sucralfate and 0.8 ml (bed volume) of Sepharose CL-6B (Pharmacia) in Tris buffer with 0.6 NNaCl. 2 μg of bFGF in 0.2 ml of saline containing 0.1 mg of BSA were loaded to the sucralfate column. The column was rinsed with 10 ml of Tris buffer with 0.6 M NaCl and eluted consecutively at a flow rate of 15 ml/hr with (i) a gradient of NaCl (80 ml) from 0.6 to 3 M; (ii) 20 ml of 3 M NaCl; and (iii) 30 ml of 1.5 M acetic acid (pH 2.2). Fractions of 2 ml were collected. Aliquots from each were diluted, neutralized with Tris buffer, and analyzed for growth factor activity as in Example I.

Figure 5:
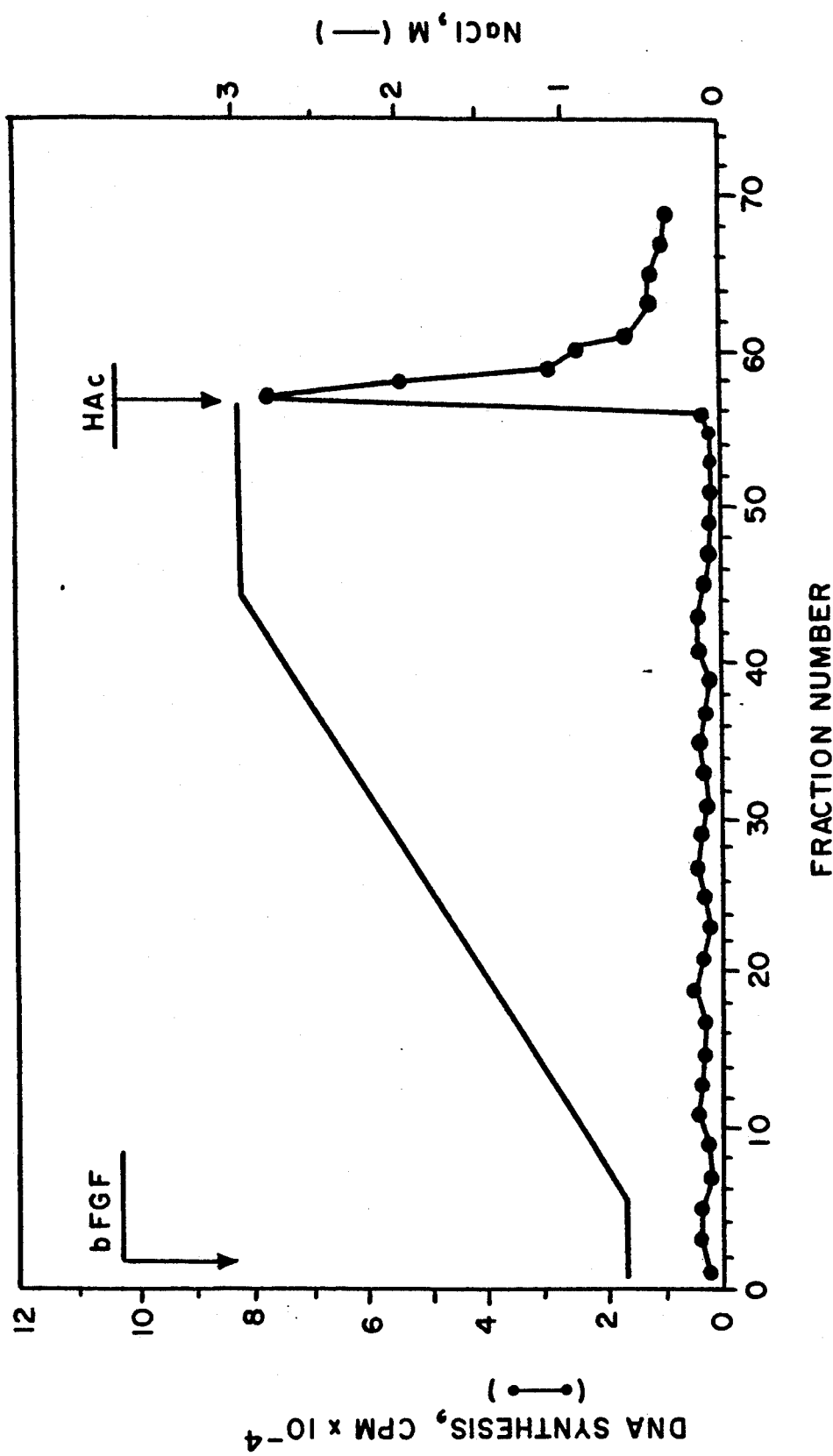
FIG. 5 illustrates the purification of bFGF from a fluid sample with a sucralfate-Sepharose column.

As can be seen from FIG. 5, when sucralfate was mixed with Sepharose beads to form a column, a gradient of NaCl up to 3M was unable to elute bFGF which had previously been loaded onto the column. Biologically active bFGF was recovered from the column with 1.5 M acetic acid (pH 2.2) and its activity analyzed by the growth factor activity assay described in Example I. This further demonstrates the strong affinity of FGF for sucralfate as well as the usefulness of sucralfate in purifying FGF from a fluid sample.

What is claimed is:

1. A method for treating a mammal having a disease which is FGF-responsive, which comprises administering to said mammal an effective amount of a pharmaceutical composition comprising SOS-stabilized FGF and a pharmaceutically acceptable carrier.

2. A method of treating a mammal having an ulcerating disease of the gastrointestinal tract which comprises administering to said mammal an effective amount of a pharmaceutical composition comprising SOS-stabilized FGF and a pharmaceutically acceptable carrier.

3. The method according to claim 1 or 2, wherein the FGF component of the composition is selected from the group of native FGF, recombinant FGF, and acid-resistant FGF.

4. The method according to claim 3, wherein the recombinant FGF comprises the rhbFGF mutein CS23.

5. The method according to claim 2, wherein the ulcerating disease of the gastrointestinal tract comprises regional ileitis.

6. The method according to claim 2, wherein the ulcerating disease of the gastrointestinal tract comprises ulcerated colitis.

7. The method according to claim 2, wherein the ulcerating disease of the gastrointestinal tract comprises a peptic ulcer.

8. The method according to claim 7, wherein the peptic ulcer is duodenal.

9. The method according to claim 7, wherein peptic ulcer is gastric.

10. The method according to claim 3, wherein the mammal is a human, the composition is administered orally and the amount of the FGF protein component of the composition is between about 0.1 μg and 30 mg per day.

11. The method according to claim 10, wherein the amount of the FGF protein component is between about 1 μg and 3 mg per day.

12. The method according to claim 10, wherein the amount of the FGF protein component is between about 10 μg and 300 μg per day.

13. The method according to claim 3, wherein the mammal is a human, the composition is administered orally and the amount of the SOS component of the composition is between about 0.1 g and 6 g/day in divided doses.

* * * * *

UNITED STATES PATENT AND TRADEMARK OFFICE
CERTIFICATE OF CORRECTION

PATENT NO. : 5,202,311
DATED     : April 13, 1993
INVENTOR(S) : Moses J. Folkman et al It is certified that error appears in the above-indentified patent and that said Letters Patent is hereby corrected as shown below:

On the title page, Item [76]: replace "Inventors: Moses J. Folkman, Brookline; Yuen Shing, Randolph, both of Mass."

with Inventors: --Moses J. Folkman, Brookline; Yuen Shing, Randolph; Sandor Szabo, Brookline, all of Mass.--

Column 4, line 35, replace "gastrointestina" with --gastrointestinal--
Column 3, line 16, replace "acceptible" with --acceptable--.
Column 4, line 5, replace "an" to --and--.
Column 5, line 1, replace "on" to --one--.
Column 5, line 35, replace "generaly" with --generally--.
Column 5, line 51, replace "it" with --its--.
Column 6, line 24, replace "duodenalulcers" to --duodenal ulcers--.
          line 39, replace "PCT/US/03467" with --PCT/US89/03467--.
Column 7, line 36, replace "upto" with --up to--.
          line 48, replace "pates" with --pages--.
Column 8, line 3, replace "klagsburn" with --klagsbrun--.
          line 65, replace "klagsburn" with --klagsbrun--.

Signed and Sealed this

Tenth Day of May, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,202,311
DATED : April 13, 1993
INVENTOR(S) : Moses J. Folkman, et al It is certified that error appears in the above-indentified patent and that said Letters Patent is hereby corrected as shown below:

Title page to Patent, Item [75], replace

"Inventors: Moses J. Folkman, Brookline; Yuen Shing, Randolph, both of Mass."

with

--Inventors: Moses J. Folkman, Brookline; Yuen Shing, Randolph; Sandor Szabo, Brookline, all of Mass.--

Title page to Patent, Item [73], replace

"Assignee: Children's Medical Center Corporation, Boston, Mass."

with

--Assignee: Children's Medical Center Corporation, Boston, Mass.; Brigham and Women's Hospital, Inc., Boston, Mass.--

Column 4, line 35, replace "gastrointestina" with --gastrointestinal--.

Signed and Sealed this

Fifth Day of July, 1994

*Attest:*

BRUCE LEHMAN

*Attesting Officer*    *Commissioner of Patents and Trademarks*